United States Patent [19]

Johnson et al.

[11] Patent Number: 4,463,092

[45] Date of Patent: Jul. 31, 1984

[54] PROCESS FOR PRODUCTION ANTIBIOTIC A53868

[75] Inventors: Ronald D. Johnson; Ralph E. Kastner, both of Indianapolis; Stephen H. Larsen, Carmel; Earl E. Ose, Greenfield, all of Ind.

[73] Assignee: Eli Lilly and Company, Indianapolis, Ind.

[21] Appl. No.: 424,805

[22] Filed: Sep. 27, 1982

[51] Int. Cl.$^3$ .................. C12P 21/02; C12N 1/20; C12R 1/465

[52] U.S. Cl. .................................................... 435/70

[58] Field of Search ............... 435/70, 172, 253, 886

[56] References Cited

U.S. PATENT DOCUMENTS

| | | | |
|---|---|---|---|
| 3,639,590 | 2/1972 | Hendlin et al. | 424/203 |
| 4,016,148 | 4/1977 | Atherton et al. | 260/112.5 R |
| 4,143,134 | 3/1979 | Atherton et al. | 424/177 |
| 4,143,135 | 3/1979 | Kuroda et al. | 435/128 |
| 4,206,156 | 6/1980 | Kamiya et al. | 260/944 |
| 4,331,591 | 5/1982 | Baylis | 260/112.5 R |

OTHER PUBLICATIONS

Derwent Abstract No. 06762E/04 (Grelan Pharmaceutical) of Japanese Unexamined Application No. J5 6161-397 (Dec. 11, 1981).
L. Maier, "Advances in the Chemistry of Aminophosphinic Acids", *Phosphorous and Sulfur*, 14, 295-296 and 320-321 (1983).
F. Atherton et al., "Phosphonopeptides as Antibacterial Agents: Rationale, Chemistry, and Structure-Activity Relationships", *Antimicrob. Agents and Chemotherapy* 15 (5), 677-683 (1979).
J. Allen et al., "Phosphonopeptides as Antibacterial Agents: " Alaphosphin and Related Phosphonopeptides, *Ibid.* 15 (5), 684-695 (1979).
T. Murakawa et al., "Pharmacokinetics of Fosmidomycin, A New Phosphonic Acid Antibiotic", *Ibid.* 21 (2), 224-230 (1982).
F. Hahn, "Alafosfalin, A New Synthetic Antibacterial Compound", *Naturwissenschaften* 68, 90 (1981).
B. Park et al., "Structure of Plumbemycin A and B, Antagonists of L-Threonine from Streptomyces plumbeus", *Agric. Biol. Chem.* 41 (3), 573-575 (1977).
F. Atherton et al., "Phosphonopeptide Antibacterial Agents Related to Alafosfalin: Design, Synthesis and Structure-Activity Relationships", *Antimicrobial Agents and Chemotherapy* 18 (6), 897-905 (1980).
Derwent No. 01051 E/01 (Grelan Pharmaceutical) of Japanese Unexamined Patent No. J5, 6156-294 (Dec. 2, 1981).
Derwent No. 46673 D/26 (Grelan Pharmaceutical) of Japanese Unexamined Patent No. J5 6051-494 (May 9, 1981).
M. Okuhara et al., "New Phosphonic Acid Antibiotics Produced by Strains of Streptomyces", *Drugs Exptl. Clin. Res.*, 7 (4), 559-564 (1981).
Y. Okada et al, "Amino Acids and Peptides v. Synthesis of N-L- and D-Alanyl-1-Amino-Ethylphosphinic Acids", *Chem. Pharm. Bull.* 28 (4), 1320-1323 (1980).
K. Hemmi et al., "Studies on Phosphonic Acid Antibiotics. IV. Synthesis and Antibacterial Activity of Analogs of 3-(N-Acetyl-N-Hydroxyamino)Propylphosphinic Acid (FR-900098)", *Ibid*, 30 (1), 111-118 (1982).

*Primary Examiner*—Lionel M. Shapiro
*Attorney, Agent, or Firm*—Nancy J. Harrison; Arthur R. Whale

[57] ABSTRACT

Antibiotic A53868 factor A, which is $N^2$-glycyl-N-(2-methylene-2-phosphonoethyl)leucinamide, and the formula:

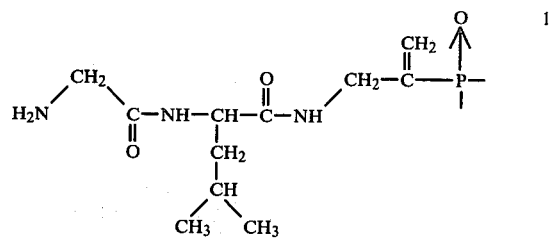

and the salts thereof, which are useful as antibiotics or as intermediates to antibiotics; methods of preparing A53868 factor A by fermentation of *Streptomyces luridus*; and the microorganism *S. luridus* NRRL 15101.

5 Claims, 1 Drawing Figure

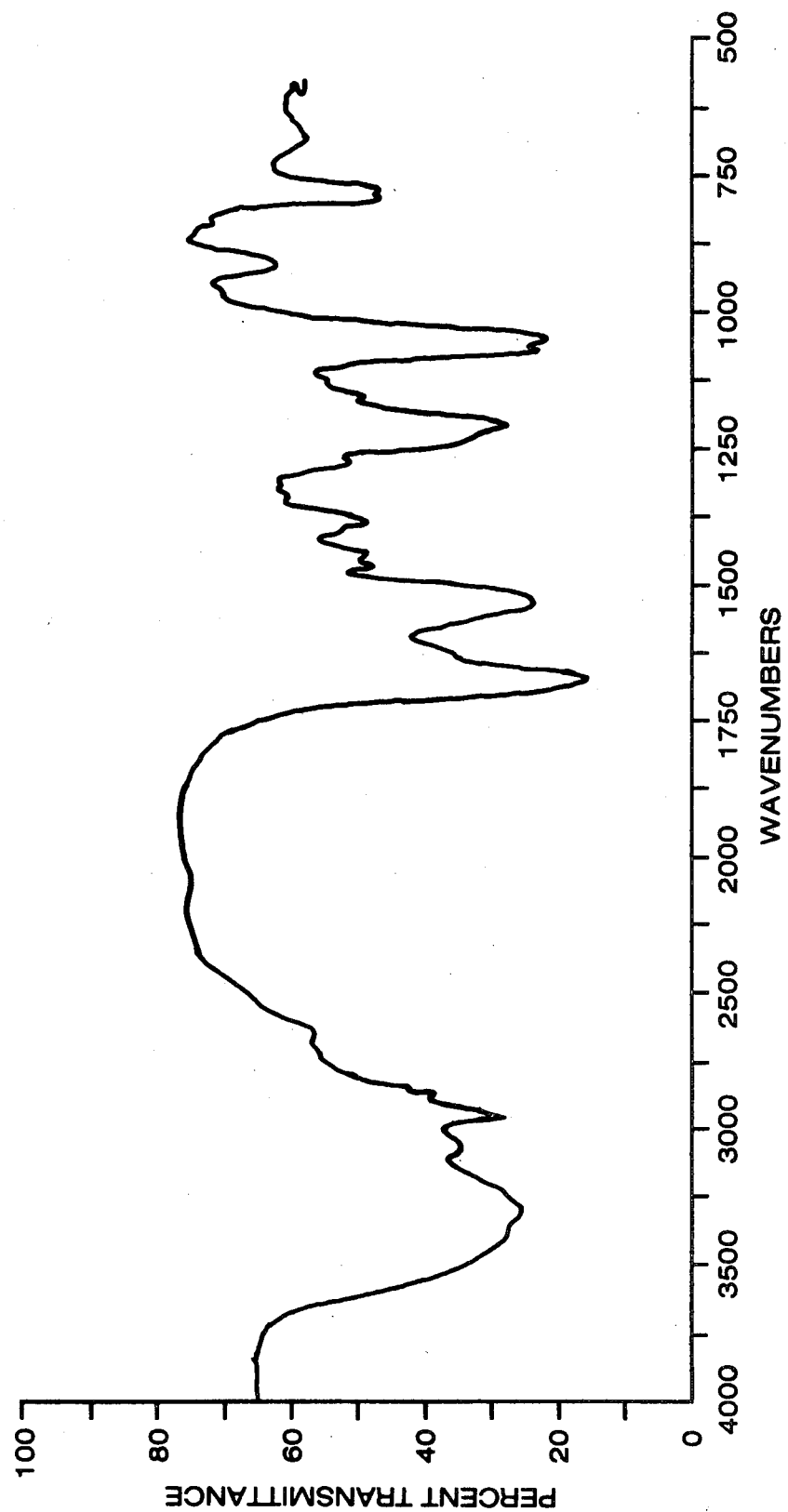

PROCESS FOR PRODUCTION ANTIBIOTIC A53868

SUMMARY OF THE INVENTION

This invention relates to a new antibiotic, called A53868 factor A, which is $N^2$-glycyl-N-(2-methylene-2-phosphonoethyl)leucinamide having formula 1:

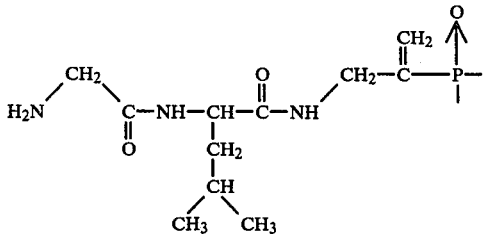

and the salts thereof. These compounds are useful as antibiotics and/or as intermediates to antibiotics. This invention also relates to a new strain of *Streptomyces luridus* and to a method of producing A53868 factor A by submerged aerobic fermentation of this microorganism.

DESCRIPTION OF THE DRAWING

The infrared absorption spectrum of A53868 factor A in KBr pellet is presented in the accompanying drawing.

DETAILED DESCRIPTION OF THE INVENTION

This invention relates to new antibiotics. In particular, this invention relates to a new antibiotic designated A53868 factor A and to its salts.

New, improved antibiotics are continually in demand. Better antibiotics are needed for treating human diseases, and improved antibiotics are also needed in the veterinary field. Increased potency, expanded spectrum of bacterial inhibition, increased in vivo efficacy, and improved pharmaceutical properties (such as greater oral absorption, higher blood or tissue concentrations, longer body half-life, and more advantageous rate or route of excretion and rate or pattern of metabolism) are some of the goals for improved antibiotics.

Antibiotic A53868 factor A is a new member of a group of phosphonopeptide antibiotics. Members of this group include alafosfalin (L-alanyl-L-1-aminoethyl-phosphonic acid) [see *Antimicrobial Agents and Chemotherapy* 18 (6), 897–905 (1980)], FR-31564 [see ibid 19 (6), 1013–1023 (1981)], and others [see European Patents 26-409 and 26-410 (Derwent No. 27620D and 27621D) and Japanese Patents J5 6051-494 (Derwent No. 46673D) and J5 6156-294 (Derwent No. 01051/E)].

Antibiotic A53868 factor A is a member of an antibiotic complex which comprises more than one factor. The A53868 complex contains major factor A and other as yet uncharacterized factors.

The term "complex" as used in the fermentation art and in this specification refers to a mixture of co-produced individual antibiotic factors. As will be recognized by those familiar with antibiotic production by fermentation, the number and ratio of individual factors produced in an antibiotic complex will vary, depending upon the fermentation conditions used. In the A53868 complex, factor A is the major factor.

The following paragraphs describe the properties of A53868 factor A.

A53868 factor A is a colorless amorphous material having an empirical formula of $C_{11}H_{22}N_3O_5P$ and a molecular weight of about 307. Elemental analysis of A53868 factor A indicates that it has the following approximate percentage composition:

|  | Found | | Calculated for |
|---|---|---|---|
|  | Sample I | Sample II | $C_{11}H_{21}N_3O_5PNa$ |
| Carbon | 41.32 | 38.74 | 40.12 |
| Hydrogen | 7.61 | 6.78 | 6.43 |
| Nitrogen | 11.53 | 12.42 | 12.76 |
| Oxygen | 24.38 | — | 24.30 |
| Phosphorus | — | 7.70 | 9.41 |
| Ash* | 13.58 | — | — |

*Ash was shown to be phosphate

Mass spectrometry of A53868 factor A, run in the fast-atom bombardment mode, gave the following results:

|  | m/Z | HRMS | Elemental Composition |
|---|---|---|---|
| M + H | 308 | 308.13818 | $C_{11}H_{23}N_3O_5P$ |
|  | 143 | 143.11878 | $C_7H_{15}N_2O$ |
|  | 138 | 138.03240 | $C_3H_9NO_3P$ |

Molecular weight = 307
Molecular formula = $C_{11}H_{22}N_3O_5P$

The infrared absorption spectrum of A53868 factor A (free acid) in KBr pellet is shown in the accompanying drawing. Significant absorption maxima occur at the following frequencies (cm$^{-1}$):

3368, 3312 and 3300 (broad, strong), 3063 (weak), 2966 (medium to weak), 2833 (very weak), 2663 (weak), 1671 (strong), 1625 (shoulder), 1536 (strong), 1469 (weak), 1442 (weak), 1386 (medium to weak), 1340 (very weak), 1277 (very weak), 1240 (shoulder), 1207 (strong), 1157 (very weak), 1068 (medium), 1048 (strong), 918 (medium to weak), 797 (medium), 778 (medium), and 625 (weak).

Amino-acid analyses on samples of A53868 factor A hydrolyzed with 6N HCl gave the following results:

| Amino Acid | µMoles/mg Found | Theoretical | Average % Purity |
|---|---|---|---|
| glycine | 2.8 | 3.2 | 87% |
| leucine | 2.86 | 3.2 | 87% |

Electrometric titration of A53868 factor A in 66% aqueous dimethylformamide indicated the presence of a titratable group with a $pK_a$ value of 8.2 (the glycyl amino group).

A53868 factor A is soluble in water and dimethyl sulfoxide and is insoluble in most organic solvents.

Nuclear magnetic resonance spectrometry of A53868 factor A, using a 360 MHz instrument with the sample dissolved in DMSO-$d_6$, indicated that A53868 factor A has the structure shown in formula 1:

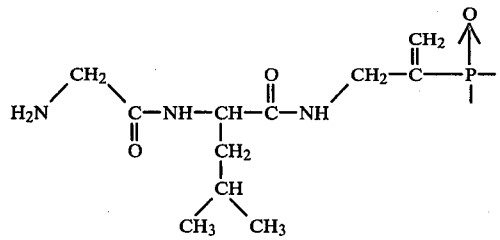

A53868 factor A is capable of forming salts. These salts are also part of this invention. It will be appreciated that A53868 factor A has both an acid function which can form salts and an amino group which can form acid-addition salts. Such salts are useful, for example, for separating and purifying the antibiotic. In addition, pharmaceutically acceptable salts are especially useful.

Pharmaceutically-acceptable alkali-metal, alkaline-earth-metal and amine salts and acid-addition salts are particularly useful. Representative and suitable alkali-metal and alkaline-earth metal salts include the sodium, potassium, lithium, cesium, rubidium, barium, calcium and magnesium salts. Suitable amine salts include the ammonium and the primary, secondary, and tertiary $C_1$–$C_4$-alkylammonium and hydroxy-$C_2$–$C_4$-alkylammonium salts. Illustrative amine salts include those formed by reaction of A53868 factor A with ammonium hydroxide, methylamine, sec-butylamine, isopropylamine, diethylamine, cyclohexylamine, diisopropylamine, cyclohexylamine, ethanolamine, triethylamine, 3-amino-1-propanol, and the like.

The alkali-metal and alkaline-earth-metal cationic salts are prepared according to procedures commonly used for the preparation of cationic salts. For example, A53868 factor A is dissolved in a suitable solvent such as water; a solution containing the stoichiometric quantity of the desired inorganic base is added to this solution, using care to prevent the pH of the solution from becoming too basic. The salt thus formed can be isolated by routine methods, such as filtration or evaporation of the solvent. Alternatively, A53868 factor A in solution can be passed over an appropriate ion-exchange resin.

The salts formed with organic amines can be prepared in a similar manner. For example, the gaseous or liquid amine can be added to a solution of A53868 factor A in a suitable solvent such as water; the solvent and excess amine can be removed by evaporation.

Representative and suitable acid-addition salts include those salts formed by standard reaction with both organic and inorganic acids such as, for example, hydrochloric, sulfuric, phosphoric, acetic, succinic, citric, lactic, maleic, fumaric, palmitic, cholic, pamoic, mucic, D-glutamic, d-camphoric, glutaric, glycolic, phthalic, tartaric, lauric, stearic, salicylic, methanesulfonic, benzenesulfonic, sorbic, picric, benzoic, cinnamic, and like acids.

The novel antibiotic of this invention is produced by culturing an A53868-factor A-producing strain of *Streptomyces luridus* under submerged aerobic conditions in a suitable culture medium until substantial antibiotic activity is produced. The antibiotic is recovered by the use of various isolation and purification procedures recognized in the fermentation art.

THE MICROORGANISM

The microorganism of this invention was studied and characterized by Frederick P. Mertz of the Lilly Research Laboratories.

The new organism useful for the preparation of A53868 factor A was isolated from a soil sample collected from Granik Rapids at the bottom of the Grand Canyon in Arizona. This organism, called culture A53868, is classified as a strain of *Streptomyces luridus*. This classification is based on a comparison with published descriptions of this species [R. E. Buchanan and N. E. Gibbons, "Bergey's Manual of Determinative Bacteriology," 8th Ed, The Williams and Wilkins Company, Baltimore, MD, 1974; E. B. Shirling and D. Gottlieb, "Cooperative Description of Type Cultures of Streptomyces," *Intern. Journal of Systematic Bacteriol.* 18 (2): 142 (1968); E. Kuster, "Simple Working Key for the Classification and Identification of Named Taxa Included in the International Streptomyces Project", ibid 22 (3): 134–148 (1972); H. Nonomura, "Key for Classification and Identification of 458 Species of the Streptomycetes Included in ISP," *J. Ferment. Technol.* 52 (2): 78–92 (1974); I. M. Szabo et al., "A Diagnostic Key for the Identification of "Species" of Streptomyces and Streptoverticillum Included in the International Streptomyces Project," *Acta Botanica Academiae Scientiarium Hungaricae* 21 (3–4), 387–418 (1975); and S. A. Waksman, "The Actinomycetes" Vol. II, The Williams and Wilkins Co., Baltimore, MD, 1961, p. 236].

This classification is based on methods recommended for the International Streptomyces Project (ISP) [E. B. Shirling and D. Gottlieb, "Methods of Characterization of Streptomyces Species," *Intern. Journal of Systematic Bacteriol.* 16 (3), 313–340 (1966)] along with certain supplementary tests.

Carbon utilization was determined with ISP #9 basal medium to which filter-sterilized carbon sources were added to equal a final concentration of 1.0%. The basal medium was sterilized by autoclaving. Plates were read after 14 days incubation at 30° C.

The cell-wall sugars were determined using a modification of the procedure of Lechevalier (M. P. Lechevalier, "Chemical Methods as Criteria for the Separation of Actinomycetes into Genera," Workshop sponsored by the Subcommittee on Actinomycetes of the American Society of Microbiology, Dr. Thomas G. Pridham, Convenor; held at the Institute of Microbiology, Rutgers University, The State University of New Jersey, New Brunswick, NJ, 1971). The isomer of diaminopimelic acid was determined using the method of Becker et al. [B. Becker, et al., "Rapid Differentiation Between Nocardia and Streptomyces by Paper Chromatography of Whole Cell Hydrolysates," *Appl. Microbiol.* 11, 421–423 (1964)].

Melanoid pigment production (chromogenicity) was determined using ISP #1 (tryptone-yeast extract broth), ISP #6 (peptone-yeast extract iron agar), ISP #7 (tyrosine agar), and modified ISP #7 (ISP #7 without tyrosine).

Starch hydrolysis was determined by testing for the presence of starch with iodine on ISP #4 (inorganic salts-starch agar) plates (D. J. Blazevic and G. M. Ederer, "Principles of Biochemical Tests in Diagnostic Microbiology," John Wiley and Sons, New York, NY, 1975, p. 99).

Temperature range and NaCl tolerance were done using ISP #2 agar medium. NaCl tolerance was measured by adding NaCl to the agar to equal the desired concentrations. These were incubated at 30° C.

ISCC-NBS Centroid Color Charts, Standard Sample No. 2106 (U.S. Department of Commerce, National Bureau of Standards, Washington, D.C., 1958) and the Color Harmony Manual (4th Ed, Color Standards Dept., Container Corp. of America, IL, 1958) were used to assign color names.

CHARACTERIZATION OF A53868-PRODUCING STRAIN

Cultural Characteristics

A53868 produces abundant aerial mycelia with a spore mass color in the red (R) color series. The nearest matching color tab for the red color series in the Tresner and Backus system [Color Harmony Manual and H. D. Tresner, and E. J. Backus, "System of Color Wheels for Streptomycete Taxonomy," *Appl. Microbiol.* 11, 335–338 (1956)] is 5ca light yellowish pink to 4ec grayish-yellowish pink. In the ISCC-NBS system, the nearest matching color chip is 31.p.y. Pink, pale yellowish pink. This cultural characteristic is produced on oatmeal agar (ISP No. 3), Czapek's-solution agar and tomato paste-oatmeal agar (TPO). It is best seen when grown on inorganic salts-starch agar (ISP No. 4).

The reverse of the colony produces no distinctive pigments. The color of the reverse side is a moderate orange yellow when grown on ISP No. 4. This color varies in shade and intensity when grown on other media. No soluble pigments are produced.

When plated for variability, this culture presented a stable homogeneous colony type. An occasional variant with no aerial hyphae was observed. This cultural information is detailed in Table I.

TABLE I
Cultural Characteristics of A53868

| Medium | | Characteristics[a] |
|---|---|---|
| ISP No. 2 | G | Abundant |
| | R | 68.S.OY |
| | Am | Abundant: 3CA Pale OY (R) |
| | Sp | None |
| ISP No. 3 | G | Good |
| | R | 33.br Pink |
| | Am | Fair: 4ec Grayish yellowish pink (R) |
| | Sp | None |
| ISP No. 4 | G | Abundant |
| | R | 71.m.OY |
| | Am | Abundant: 5CA Light yellowish pink (R) |
| | Sp | None |
| ISP No. 5 | G | Abundant |
| | R | 86.1.Yellow |
| | Am | Abundant: a White (W) |
| | Sp | None |
| Czapek's Agar | G | Fair |
| | R | 73.p.OY (very pale) |
| | Am | Fair: 3CA p.OY to 4ec gy.yPK (R) |
| | Sp | None |
| TPO | G | Abundant |
| | R | 72.d.OY |
| | Am | Abundant: 3CA p.OY to 5cb gy.yPK (R) |
| | Sp | None |

[a] G = growth
R = reverse
Am = aerial mycelia
Sp = soluble pigment

Morphological Characteristics

Culture A53868 produces well-developed, non-fragmenting aerial mycelia which are monopodially branched. Sporophores are of moderate length and are arranged as hooks and open loops of wide diameter. Occasional primitive spirals are also observed. When present, they are short, tight and compact. Sporophore morphology is placed in the section Retinaculiaperti (RA) of Pridham, et al., supra.

This morphology is best observed on ISP No. 4 and Czapek's solution agar. Mature spore chains generally contain about 10 spores per chain. The spore shape is spherical to oblong, but is mainly oblong. The spore size was determined with an optical light microscope, using a Vickers Image Splitting Measuring Eyepiece. The spore size ranges from 0.93–1.85 $\mu M$ in length and 0.62–1.30 $\mu M$ in width. The average size is 1.28 $\mu M \times 0.94$ $\mu M$. The spore surface ornamentation is smooth.

Physiological Characteristics

Analysis of hydrolyzed whole cells demonstrated the presence of LL-DAP (diaminopimelic acid) with no meso isomer present. Sugar analysis of hydrolyzed whole cells demonstrated the presence of glucose, mannose and ribose. This represents a Type I cell wall and an NC, or no-characteristic, sugar pattern (see "Bergey's Manual", supra). This combination of major cell-wall constituents is indicative of the genus Streptomyces.

The carbon utilization pattern for A53868 is as follows: L-arabinose, D-glucose, cellobiose, D-fructose, D-galactose, i-inositol, lactose, D-maltose, D-ribose, salicin, sodium acetate, sodium citrate, sodium succinate, and D-xylose are all utilized for growth. D-arabinose, melibiose, D-mannitol, D-raffinose, L-rhamnose, and sucrose do not support growth.

Culture A53868 will liquefy gelatin and hydrolyze starch. It does not reduce nitrate. Skim milk is neither hydrolyzed nor peptonized by the culture.

Culture A53868 will tolerate up to 7 percent NaCl and will grow at temperatures between 10°–37° C.

Melanoid pigments are produced by A53868 when grown in tryptone-yeast extract broth (ISP No. 1), and on slants of peptone-yeast extract-iron agar (ISP No. 6) and tyrosine agar (ISP No. 7).

Species Determination

The cultural, morphological and physiological characteristics of A53868 were compared with published descriptions of similar species. Fourteen Streptomyces species had close resemblance to culture A53868 and were, therefore, studied in detail. Two species were selected as being the most similar to A53868. These two cultures are:

*Streptomyces lavendofoliae* (E. B. Shirling, et al., supra, p. 339)

*Streptomyces luridus* (E. B. Shirling, et al., supra, p. 142)

These two cultures are reported in the literature as belonging in the red (R) color series with retinaculiaperti (RA) sporophore morphology, smooth (Sm) spore-surface ornamentation, producing melanoid pigments and having a carbon-utilization pattern and other characteristics quite similar to A53868. They are both recognized in the Approved List of Bacterial Names [V.B.D. Skerman et al., *Intern. Journal of Systematic Bacteriol.* 30 (1), 225–420 (1980)].

Further comparison of culture A53868 with these two cultures shows:

*S. lavendofoliae:* This culture has many characteristics in common with A53868; and, although the differences are few, they are more than those with *S. luridus*. The general morphology, pigmentation, lack of soluble pigments, production of melanoid pigment, spore-mass color, spore-surface ornamentation and carbon utilization are all similar to A53868. *S. lavendofoliae* differs from A53868 in having a longer spore chain, more spiral sporophores, lack of fructose utilization, and poorer growth on Czapek's solution agar.

*S. luridus:* This culture is similar culturally, morphologically and physiologically to A53868. Both cultures are in the Red (R) color series, lack distinctive pigments, have the same (RA) sporophore morphology with smooth spore surface, produce melanoid pigments, and have a similar carbon utilization pattern. The similarities and differences between A53868 and *S. luridus* are summarized in Table II. Tables III and IV give more detailed comparisons between A53868 and *S. luridus*.

TABLE II

| Comparison of Culture A53868 and *S. luridus* | |
|---|---|
| Similarities | Differences |
| Aerial spore mass color (R) | Gelatin liquefaction |
| Carbon-utilization pattern | NaCl tolerance |
| Cultural characteristics | Nitrate reduction |
| Distinctive pigments absent | Skim-milk reaction |
| Melanoid pigments produced | Utilization of fructose |
| Morphology (RA) | |
| Soluble pigments absent | |
| Spore-chain length (10–50) | |
| Spore shape | |
| Spore-surface ornamentation | |
| Starch hydrolysis | |

TABLE III

| Utilization of Carbon Compounds by Culture A53868 and *S. luridus*[a] | | |
|---|---|---|
| Carbon Source | A53868 | S. luridus |
| No carbon | − | − |
| L-arabinose | + | + |
| D-fructose | + | ± |
| D-glucose | + | + |
| i-inositol | + | + |
| D-mannitol | − | − |
| raffinose | − | − |
| L-rhamnose | − | − |
| sucrose | − | − |
| D-xylose | + | + |
| D-arabinose | − | ND[b] |
| cellobiose | + | ND |
| D-galactose | + | ND |
| lactose | + | ND |
| D-maltose | + | ND |
| melibiose | − | ND |
| Na-acetate | + | ND |
| Na-citrate | ± | ND |
| Na-succinate | + | ND |
| ribose | + | ND |
| salicin | + | ND |

[a] − = no utilization
+ = utilization
± = doubtful utilization

TABLE IV

| Comparison of A53868 and *S. luridus* | | |
|---|---|---|
| Characteristic | A53868 | S. luridus |
| Aerial spore mass color | Red | Red |
| Carbon-utilization pattern | + | + |
| (D-fructose) | + | ± |
| Cell-wall type | ± | ND[a] |
| Gelatin liquefaction | + | − |
| Melanoid pigment | + | + |
| ISP No. 1 | + | + |
| ISP No. 6 | + | + |
| ISP No. 7 | + | + |

TABLE IV-continued

| Comparison of A53868 and *S. luridus* | | |
|---|---|---|
| Characteristic | A53868 | S. luridus |
| ISP No. 7 mod. | − | ND |
| Morphology | RA | RA |
| NaCl tolerance - percent | 7 | <7 |
| Nitrate reduction | − | + |
| Reverse side color | OY | OY |
| Skim milk | − | + |
| Soluble pigments | − | − |
| Spore shape | Oblong | Oblong |
| Spore surface | Sm | Sm |
| Starch hydrolysis | + | + |
| Temperature range - °C. | 10–37 | ND |

[a] ND = not done

These comparisons indicate that A53868 is very similar to *S. luridus*. Culture A53868 is, therefore, classified as a strain of *Streptomyces luridus* (Krasilnikov, Korenyako, Meksina, Valedinskaya and Veselov) Waksman 1961. This classification was based on a comparison with published descriptions and not on direct laboratory comparisons.

The *Streptomyces luridus* culture useful for the production of A53868 factor A has been deposited and made a part of the stock culture collection of the Northern Regional Research Center, U.S. Department of Agriculture, Agricultural Research Service, Peoria, Ill., 61604, from which it is available to the public under the name NRRL 15101.

As is the case with other organisms, the characteristics of the A53868-factor-A-producing culture, *Streptomyces luridus* NRRL 15101, are subject to variation. For example, variants, recombinants, and mutants of the NRRL 15101 strain may be obtained by treament with various known mutagens such as ultraviolet rays, X-rays, high-frequency waves, radioactive rays and chemicals. All natural and induced variants, mutants and recombinants of *Streptomyces luridus* NRRL 15101 which produce A53868 factor A may be used in this invention.

The culture medium used to grow *Streptomyces luridus* NRRL 15101 can be any one of a number of media. For economy in production, optimal yield, and ease of product isolation, however, certain culture media are preferred. Thus, for example, a preferred carbon source in large-scale fermentation is soluble starch, although glucose, starch, dextrin, glycerol, and the like can also be used. A preferred nitrogen source is pancreatic digest of casein, although enzyme-hydrolyzed casein, enzymatic digest of soy meal, acid-hydrolyzed casein, and the like are also useful. Glycine and leucine enrichment of the medium may also be beneficial.

Nutrient inorganic salts which can be incorporated in the culture media are the soluble salts capable of yielding calcium potassium, ammonium, chloride, sulfate, nitrate, phosphate, and like ions.

Essential trace elements necessary for the growth and development of the organism should also be included in the culture medium. Such trace elements commonly occur as impurities in other constituents of the medium in amounts sufficient to meet the growth requirements of the organism.

It may be necessary to add small amounts (e.g., 0.2 ml/L) of an antifoam agent such as polypropylene glycol to large-scale fermentation media if foaming becomes a problem.

For production of substantial quantities of A53868 factor A, submerged aerobic fermentation in tanks is preferred. Small quantities of A53868 factor A may be obtained by shake-flask culture. Because of the time lag in antibiotic production commonly associated with inoculation of large tanks with the spore form of the organism, it is preferable to use a vegetative inoculum. The vegetative inoculum is prepared by inoculating a small volume of culture medium with the spore form or mycelial fragments of the organism to obtain a fresh, actively growing culture of the organism. The vegetative inoculum is then transferred to a larger tank.

The A53868-factor-A-producing organism can be grown at temperatures between about 10° and about 37° C. Optimum A53868 factor A production appears to occur at temperatures of about 28°-30° C.

As is customary in aerobic submerged culture processes, sterile air is dispersed through the culture medium. For efficient production of A53868 factor A, the dissolved oxygen level should be maintained above 30% of air saturation (at 30° C. and atmospheric pressure).

For tank fermentation, it is preferable to maintain the pH level of the fermentation medium in a range of from about 6.5-7.4. This can be done by the addition of appropriate amounts of, for example, sodium hydroxide or hydrochloric acid.

Production of A53868 factor A can be followed during the fermentation by testing samples of the broth or of extracts of the mycelial solids for antibiotic activity against organisms known to be sensitive to the antibiotic. One assay organism useful in testing this antibiotic is *Micrococcus luteus*. The bioassay is preferably performed by paper-disc assay on agar plates.

Following its production under submerged aerobic fermentation conditions, A53868 factor A can be recovered from the fermentation medium by methods recognized in the fermentation art. The antibiotic activity produced during fermentation of an A53868-factor-A-producing organism generally occurs in the broth. Maximum recovery of A53868 factor A is accomplished, therefore, by an initial filtration to remove the mycelial mass. The filtered broth can be purified by a variety of techniques to give the A53868 complex. A preferred method involves adsorption on a carbon column, eluting to give the A53868 complex.

Further purification and separation of the A53868 complex to give the individual A53868 factor A includes additional adsorption and extraction procedures. Useful adsorptive materials for the purification of the A53868 complex and A53868 factor A include: (1) high porous polymer (Diaion HP-20); (2) Sephadex A25 and G-50; Bio-Gel P-2 and P-10; (3) Anion-exchange resins—(a) strongly basic; polystyrene, BioRad AG 1 & 2, Bio-Rex, Dowex 1 and 2, Amberlite IRA 400, 401, 410; (b) moderately basic; epoxypolyamine Bio-Rex 5, and Duolite A30B; (c) weakly basic; polystyrene or phenolic polyamine Bio-Rad AG3, Duolite A-6, A-7, Amberlite IRA 68, IR-45, IR-4B; (4) silica gel; (5) florisil; (6) polymeric adsorbents (XAD-2 and 4); (7) reversed-phase resins, silica gel/$C_{18}$ and silica gel/$C_8$; (8) carbon; (9) DEAE cellulose, DEAE Sephadex; (10) polyamide; (11) alumina; and (12) microcellulose. Sources: Bio-Rad and Bio-Gel resins—Bio Rad Laboratories, Richmond, CA; Amberlite and XAD resins—Rohm and Haas Co, Philadelphia, PA; Duolite resins—Diamond Shamrock Chemical Co, Redmond City, CA; Sephadex resins—Pharmacia Fine Chemicals AB, Uppsala, Sweden, Dowex resins—Dow Chemical Co., Midland, MI; Diaion-Mitsubishi Chemical Industries Ltd., Tokyo, Japan; XAD resins, silica gel/$C_{18}$ and silica gel/$C_8$—E. Merck, Darmstadt, Germany.

A53868 factor A and its salts inhibit the growth of certain pathogenic organisms, particularly certain gram-negative bacteria. This activity can be demonstrated in vitro, using standard agar-plate disc-diffusion tests. Table V summarizes these results of such tests with A53868 factor A in the monophosphonate monoammonium salt form. Activity is measured by the size (diameter in mm) of the observed zone in which growth of the microorganism is inhibited by the test compound.

TABLE V

| Antibacterial Activity of A53868 Factor A by the Agar-Plate Disc-Diffusion Test[a] | |
|---|---|
| Organism | Size of Zone of Inhibition (mm) |
| *Micrococcus luteus* | 28 |
| *Proteus vulgaris* | 42[b] |
| *Salmonella gallinarum* | 12[b] |
| *Escherichia coli* | 18[b] |
| *Escherichia coli*[c] | 30 |
| *Bacillus subtilis* | —[d] |
| *Bacillus subtilis*[c] | 28 |

[a] compound was dissolved in water at a concentration of 1 mg/ml; a 7-mm disc was dipped into the suspension and then placed on the agar surface; cultures were incubated 24–48 hrs. at 25-37° C.
[b] overgrowth noted
[c] grown on minimal nutrient agar
[d] no observable zone A53868 factor A has shown antibacterial activity in vivo in tests with one-day-old chicks infected intramuscularly with *Salmonella typhimurium*. The results of a representative test are summarized in Table VI.

TABLE VI

| Antibacterial Activity of A53868 Factor A vs. *Salmonella typhimurium* in Day-Old Chicks | | | | |
|---|---|---|---|---|
| Treatment[a] | | No Died/No. in Group | | |
| (mg/kg) | Day 2 | 3 | 4 | 5 |
| 0 | 1/20 | 17/20 | 17/20 | 19/20 |
| 30 | 1/20 | 18/20 | 18/20 | 18/20 |
| 60 | 1/20 | 9/20 | 14/20 | 14/20 |

[a] administered (subcutaneously) six hours prior to challenge of chicks with *S. typhimurium*.

This invention also relates to methods of controlling infections caused by Samonella species. In carrying out the methods of this invention, an effective amount of a compound of formula 1 is administered parenterally to an infected or susceptible warm-blooded animal.

The dose which is effective to control the infection will vary with the severity of the infection and the age, weight, and condition of the animal. The total dose required for protection parenterally will generally, however, be in the range of from about 20 to about 200 mg/kg and preferably will be in the range of from about 40 to about 100 mg/kg.

In another aspect, this invention relates to compositions useful for the control of infections caused by Salmonella species. These compositions comprise a compound of formula 1 together with a suitable vehicle. Compositions may be formulated for parenteral administration by methods recognized in the pharmacetical art.

Effective injectable compositions containing these compounds may be in either suspension or solution form. In the preparation of suitable formulations it will be recognized that, in general, the water solubility of the salts is greater than that of A53868 factor A itself.

In the solution form the compound is dissolved in a physiologically acceptable vehicle. Such vehicles comprise a suitable solvent, preservatives such as benzyl alcohol, if needed, and buffers. Useful solvents include, for example, water and aqueous alcohols, glycols, and carbonate esters such as diethyl carbonate. Such aqueous solutions contain, in general, no more than 50% of the organic solvent by volume.

Injectable suspension compositions require a liquid suspending medium, with or without adjuvants, as a vehicle. The suspending medium can be, for example, aqueous polyvinylpyrrolidone, inert oils such as vegetable oils or highly refined mineral oils, or aqueous carboxymethylcellulose.

Suitable physiologically acceptable adjuvants are necessary to keep the compound suspended in suspension compositions. The adjuvants may be chosen from among thickeners such as carboxymethylcellulose, polyvinylpyrrolidone, gelatin, and the alginates. Many surfactants are also useful as suspending agents. Lecithin, alkylphenol polyethylene oxide adducts, naphthalenesulfonates, alkylbenzenesulfonates, and the polyoxyethylene sorbitan esters are useful suspending agents.

Many substances which affect the hydrophilicity, density, and surface tension of the liquid suspending medium can assist in making injectable suspensions in individual cases. For example, silicone antifoams, sorbitol, and sugars can be useful suspending agents.

In order to illustrate more fully the operation of this invention, the following examples are provided.

EXAMPLE 1

Preparation of A53868

A. Shake-flask Fermentation of A53868

A lyophilized pellet of *Streptomyces luridus* NRRL 15101 is dissolved in 1-2 ml of sterilized water. This solution is used to inoculate an agar slant having the following composition:

| Ingredient | Amount (%) |
| --- | --- |
| Beef Extract | 0.05 |
| Glucose | 1.25 |
| Corn Starch | 0.5 |
| Potato Dextrin | 0.5 |
| Yeast Extract | 0.05 |
| Enzymatic Hydrolysate of casein[a] | 0.03 |
| Soluble Meat Peptone[b] | 0.5 |
| Blackstrap Molasses | 0.25 |
| $MgSO_4.7H_2O$ | 0.025 |
| Czapek's Mineral Stock[c] | 0.2 |
| Deionized water | q.s. 1 liter |
| Presterile pH adjusted to 7.5 with 5N NaOH; poststerilization pH 6.8. | |
| [a]NZ Amine A, Humko Sheffield Chemical, Lyndhurst, NJ. | |
| [b]O.M. Peptone, Amber Laboratories, Juneau, WI 53039. | |
| [c]Czapek's Mineral Stock has the following composition: | |
| KCl | 10% |
| $MgSO_4.7H_2O$ | 10% |
| $FeSO_4.7H_2O$ | 2% (dissolved in 2 ml of conc. HCL) |
| Deionized water | q.s. to 1 liter |

The inoculated slant is incubated at 30° C. for about seven to fourteen days. The mature slant culture is covered with sterile distilled water (10 ml) and scraped with a sterile pipette to loosen the spores. A portion (0.5 ml) of the resulting suspension of spores is used to inoculate 50 ml of a vegetative medium having the following composition:

| Ingredient | Amount (%) |
| --- | --- |
| Glucose | 1.5 |
| Potato Dextrin | 2.0 |
| Soybean Grits | 1.5 |
| Yeast Extract | 0.1 |
| Corn-Steep Liquor | 1.0 |
| $CaCO_3$ | 0.2 |
| Cold Tap Water | q.s. to 1 liter |
| Presterilization pH of about 5.6 adjusted to 6.5 with 5N NaOH; poststerilization pH 6.5–6.7. | |

The inoculated vegetative medium is incubated in a 250-ml Erlenmeyer flask at 30° C. for about 48 hours on a rotary shaker orbiting in a two-inch (5.08 cm) circle at 250 rpm.

Vegetative cultures have been successfully initiated with agar-slant cultures, with cultures preserved in liquid nitrogen and with lyophilized pellets of the culture.

Incubated vegetative medium (0.8 to 2%, volume/volume) is used to inoculate 50 ml of a production medium having the following composition:

| Ingredient | Amount (%) |
| --- | --- |
| Soluble Starch | 3.0 |
| Pancreatic Digest of Casein | 1.0 |
| $MgSO_4.7H_2O$ | 0.05 |
| $K_2HPO_4$ | 0.05 |
| Ammonium Molybdate | 0.01 |
| $CaCO_3$ | 0.2 |
| Czapek's Mineral Stock[a] | 0.2 (2 ml/liter) |
| Deionized Water | q.s. to 1 liter |
| [a]See Agar-slant medium, footnote (c) | |

The inoculated production medium was incubated in a 250-ml Erlenmeyer flask at 30° C. for 3-5 days on a two-inch rotary shaker at 250 rpm.

B. Tank Fermentation of A53868

In order to provide a larger volume of inoculum, 10 ml of incubated vegetative medium prepared as described above is used to inoculate 400 ml of a second-stage vegetative growth medium having the same composition as that of the vegetative medium. This second-stage medium is incubated in a two-liter flask for 48 hours at 30° C. on a two-inch rotary shaker at 250 rpm.

Incubated second-stage vegetative medium (2 L) thus prepared is used to inoculate 100 liters of sterile production medium having the same composition given in Section A. The inoculated production medium is allowed to ferment in a 165-liter fermentation tank for about 4-6 days at a temperature of 30° C. The fermentation medium is stirred with conventional agitators and aerated with sterile air at a rate sufficient to maintain a dissolved oxygen level greater than 30% of air saturation at atmospheric pressure.

EXAMPLE 2

Separation of A53868

Fermentation broth (200 ml), obtained as described in Example 1 was filtered, using a filter aid (2%, Hyflo, Johns-Manville Products Corp.). The mycelia were discarded, and the filtered broth was adsorbed onto a 16-liter Diaion HP-20 column (Mitsubishi Ind.). The column was eluted with 150 liters of acetonitrile:water (1:9), collecting 4-liter fractions. Elution of A53868 factor A [glycyl-leucyl-2-amino-2-propenyl-1-phosphonic acid] was monitored by an HPLC assay. In this assay the compound was eluted from a ¼"-×30-cm Zorbax ODS (12μ) column at 5.1 minutes under the following conditions:

flow rate=2.0 ml/min
detection=UV at 254 nm
sensitivity=0.16 Absorbance Units Full Scale
elution solvent=8% CH₃CN in 0.1% phosphate buffer, pH=3

The desired fractions were concentrated in vacuo, removing the acetonitrile to give an aqueous solution containing 167 g (the concentration was determined by weighing dried aliquots) of crude product.

A portion of the aqueous crude product (50 g) was placed on a two-liter HP-20 column. The column was washed with water containing 10% NaCl (4 L) and then was eluted with acetonitrile:water (1:9), collecting 200-ml fractions. The fractions were analyzed by HPLC assay. The active fractions combined and concentrated under vacuum to remove acetonitrile and give additional aqueous concentrate containing about 15 g of crude product.

Portions of the aqueous concentrates (8–10 g) or the original HP-20 aqueous crude product were placed on a two-liter LP-1/C₁₈ preparative reverse-phase HPLC column, prepared as described by Abbott et al. in U.S. Pat. No. 4,287,120, issued Sept. 1, 1981 (see Examples 6–7). After the column was washed with water (2 L), it was eluted with a solution of acetonitrile:water (5:95) plus 0.1% acetic acid (pH=3) at a flow rate of 120 ml/min, collecting 80-ml fractions which were assayed by HPLC. Elution progress was monitored by UV at 254 nm. The desired fractions were combined and lyophilized to give more purified product (2–4 g).

This product was further purified as follows: Portions (1 g) were chromatographed over a one-liter Zorbax ODS (12μ, DuPont) preparative HPLC reverse-phase column, eluting with a solution of acetonitrile:water (5:95) plus 0.1% acetic acid (pH=3) at a flow rate of 50 ml/min and collecting 25-ml fractions. Elution was monitored by UV at 254 nm, and fractions were analyzed by HPLC at 225 nm. The desired fractions were combined and lyophilized to dryness to give 200–500 mg of purified material (85–95% pure).

The total yield of this material from 200 liters of fermentation broth was 5–6 g.

The purified material was subjected to a limulus ameobocyte lysate (LAL) test for endotoxin. If the test was positive, the material was filtered at 1 mg/ml in water through a Zeta Por filter (AMF CUNO, Meriden, CT) to remove the endotoxin. The filtrate was lyophilized to dryness to give a total of 1.5–2.8 g of purified endotoxin-free A53868 factor A.

Endotoxin was also removed by hollow-fiber bundle dialysis into sterile pyrogen-free water. The material (about 500 mg) was dissolved in water (5 ml). This solution was cycled continuously through a 44-fiber Spectra Por HF hollow fiber bundle (Spectrum Medical Industries, Inc., New York, NY) with a molecular weight cut off of 5000 daltons. The hollow-fiber bundle was installed in a Fleaker hollow-fiber bundle dialysis apparatus (Corning Glass Works, Corning, NY) filled with 300 ml of sterile pyrogen-free water. The concentrate was cycled continuously through the hollow-fiber bundle at a rate of 1 ml/min, using an FMI pump (model RP, Fluid Metering Co., Oyster Bay, NY).

We claim:

1. The method of producing A53868 factor A of the formula

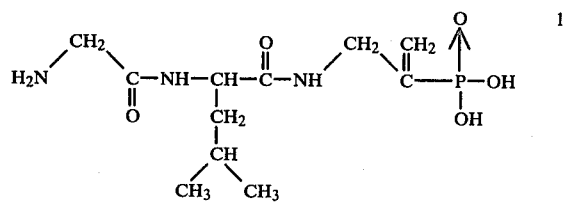

which comprises cultivating *Steptomyces luridus* NRRL 15101 or a mutant or recombinant thereof which produces A53868 factor A in a culture medium containing assimilable sources of carbon, nitrogen, and inorganic salts under submerged aerobic fermentation conditions until a substantial amount of antibiotic activity is produced.

2. The method of claim 1 which comprises cultivating *Streptomyces luridus* NRRL 15101.

3. The method of claim 1 or 2 which includes the additional step of isolating A53868 factor A.

4. A biologically pure culture of the microorganism *Streptomyces luridus* NRRL 15101 or a mutant or recombinant thereof which produces A53868 factor A of formula 1 in claim 1.

5. A biologically pure culture of the microorganism *Streptomyces luridus* NRRL 15101 of claim 4.

* * * * *

UNITED STATES PATENT AND TRADEMARK OFFICE
CERTIFICATE OF CORRECTION

PATENT NO. : 4,463,092
DATED : July 31, 1984
INVENTOR(S) : Ronald D. Johnson, Ralph E. Kastner, Stephen H. Larsen and Earl E. Ose It is certified that error appears in the above—identified patent and that said Letters Patent is hereby corrected as shown below:

Front page, second column, and columns 1 and 3, that portion of the structural formula appearing as " 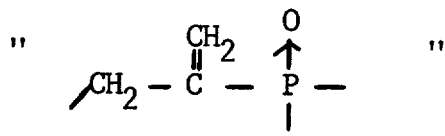 "

should read

-- 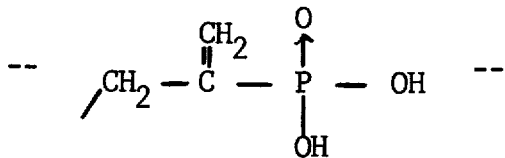 --

Column 7, line 57, insert as footnote after Table III, "$^b$ND = not done".

Column 10, line 46, "Samonella" should read -- Salmonella --.

Signed and Sealed this

Eighteenth Day of February 1986

[SEAL]

Attest:

DONALD J. QUIGG

Attesting Officer

Commissioner of Patents and Trademarks